United States Patent
Dultz et al.

(10) Patent No.: US 7,867,783 B2
(45) Date of Patent: *Jan. 11, 2011

(54) APPARATUS AND METHOD FOR PERFORMING LIGAND BINDING ASSAYS ON MICROARRAYS IN MULTIWELL PLATES

(75) Inventors: Shane C. Dultz, Westlake Village, CA (US); Jeffrey C. Travis, San Diego, CA (US); David Ralin, South Pasadena, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 753 days.

This patent is subject to a terminal disclaimer.

(21) Appl. No.: 11/677,674

(22) Filed: Feb. 22, 2007

(65) Prior Publication Data

US 2008/0207463 A1     Aug. 28, 2008

(51) Int. Cl.
*G01N 33/543* (2006.01)

(52) U.S. Cl. .................... 436/518; 422/56; 422/58; 436/524; 436/525; 436/527; 436/809

(58) Field of Classification Search ............ 422/56, 422/58; 436/518, 524, 525, 527, 809
See application file for complete search history.

(56) References Cited

U.S. PATENT DOCUMENTS

| | | |
|---|---|---|
| 1,637,141 A | 7/1927 | Cooper |
| 3,858,616 A | 1/1975 | Thiery et al. |
| 4,238,565 A | 12/1980 | Hornby et al. |
| 4,256,834 A | 3/1981 | Zuk et al. |
| 4,508,832 A | 4/1985 | Carter et al. |
| 5,164,589 A | 11/1992 | Sjoedin |
| 5,225,164 A | 7/1993 | Astle |
| 5,229,833 A | 7/1993 | Stewart |
| 5,234,769 A | 8/1993 | Shevlin |
| 5,255,075 A | 10/1993 | Cush |
| 5,313,264 A | 5/1994 | Ivarsson et al. |

(Continued)

FOREIGN PATENT DOCUMENTS

AU            742417          2/2000

(Continued)

OTHER PUBLICATIONS

Tadashi Saitoh, et al."Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

(Continued)

*Primary Examiner*—Christopher L Chin
(74) *Attorney, Agent, or Firm*—Haynes and Boone, LLP (57) ABSTRACT

An apparatus and method for real time, label-free imaging and quantitation of binding events at an array of positions are provided. Total internal reflection from a planar side wall of a well of a multiwell plate is used to create an evanescent field in the plane of a pattern of ligands immobilized on the wall. Embodiments include imaging and multiple analyte detection and quantitation of a single wall of a single well as well as the simultaneous imaging and multiple analyte detection and quantitation of a number of wells.

17 Claims, 6 Drawing Sheets

U.S. PATENT DOCUMENTS

| | | | |
|---|---|---|---|
| 5,341,215 A | 8/1994 | Seher | |
| 5,437,840 A | 8/1995 | King et al. | |
| 5,446,534 A | 8/1995 | Goldman | |
| 5,483,346 A | 1/1996 | Butzer | |
| 5,485,277 A | 1/1996 | Foster | |
| 5,491,097 A | 2/1996 | Ribi et al. | |
| 5,491,556 A | 2/1996 | Stewart et al. | |
| 5,573,956 A | 11/1996 | Hanning | |
| 5,593,130 A | 1/1997 | Hansson et al. | |
| 5,633,724 A | 5/1997 | King et al. | |
| 5,641,640 A | 6/1997 | Hanning | |
| RE35,716 E | 1/1998 | Stapleton et al. | |
| 5,738,825 A | 4/1998 | Rudigier et al. | |
| 5,753,518 A | 5/1998 | Karlsson | |
| 5,796,858 A | 8/1998 | Zhou et al. | |
| 5,813,439 A | 9/1998 | Herrero et al. | |
| 5,856,873 A | 1/1999 | Naya et al. | |
| 5,922,594 A | 7/1999 | Loefas | |
| 5,922,604 A | 7/1999 | Stapleton et al. | |
| 5,955,729 A | 9/1999 | Nelson et al. | |
| 5,965,456 A | 10/1999 | Malmqvist et al. | |
| 5,972,612 A | 10/1999 | Malmqvist et al. | |
| 6,008,010 A | 12/1999 | Greenberger et al. | |
| 6,008,893 A | 12/1999 | Roos et al. | |
| 6,026,053 A | 2/2000 | Satorius | |
| 6,045,996 A | 4/2000 | Cronin et al. | |
| 6,065,501 A | 5/2000 | Feret et al. | |
| 6,127,183 A | 10/2000 | Ivarsson et al. | |
| 6,140,044 A | 10/2000 | Bessemer et al. | |
| 6,143,513 A | 11/2000 | Loefas | |
| 6,143,574 A | 11/2000 | Karlsson et al. | |
| 6,197,595 B1 | 3/2001 | Anderson et al. | |
| 6,200,814 B1 | 3/2001 | Malmqvist et al. | |
| 6,207,381 B1 | 3/2001 | Larsson et al. | |
| 6,253,793 B1 | 7/2001 | Dupoiron et al. | |
| 6,277,330 B1 | 8/2001 | Liu et al. | |
| 6,289,286 B1 | 9/2001 | Andersson et al. | |
| 6,354,333 B1 | 3/2002 | Dupoiron et al. | |
| 6,355,429 B1 | 3/2002 | Nygren et al. | |
| 3,415,825 A1 | 7/2002 | Yoshikazu | |
| 6,475,809 B1 | 11/2002 | Wagner et al. | |
| 6,493,097 B1 | 12/2002 | Ivarsson | |
| 6,503,760 B2 | 1/2003 | Malmqvist et al. | |
| D472,644 S | 4/2003 | Dawson et al. | |
| 6,549,011 B2 | 4/2003 | Flatt | |
| 6,589,798 B1 | 7/2003 | Loefas | |
| 6,594,011 B1 | 7/2003 | Kempen | |
| D480,149 S | 9/2003 | Dawson et al. | |
| 6,698,454 B2 | 3/2004 | Sjoelander et al. | |
| 6,710,870 B1 | 3/2004 | Marowsky et al. | |
| 6,714,303 B2 | 3/2004 | Ivarsson | |
| 6,806,051 B2 | 10/2004 | Ellson | |
| 6,810,286 B2 | 10/2004 | Donovan et al. | |
| 6,833,920 B2 | 12/2004 | Rassman et al. | |
| 6,859,280 B2 | 2/2005 | Kempen | |
| 6,882,420 B2 | 4/2005 | Rassman et al. | |
| 6,981,526 B2 | 1/2006 | Glejbol et al. | |
| 7,045,287 B2 | 5/2006 | Smith et al. | |
| 7,193,711 B2 | 3/2007 | Rassman et al. | |
| 7,195,872 B2 * | 3/2007 | Agrawal et al. | 435/6 |
| 2002/0019019 A1 | 2/2002 | Hamalainen et al. | |
| 2002/0154311 A1 | 10/2002 | Ivarsson | |
| 2002/0182717 A1 | 12/2002 | Karlsson | |
| 2003/0022388 A1 | 1/2003 | Roos et al. | |
| 2003/0067612 A1 | 4/2003 | Ivarsson | |
| 2003/0112432 A1 | 6/2003 | Yguerabide et al. | |
| 2003/0148401 A1 | 8/2003 | Agrawal et al. | |
| 2003/0205681 A1 | 11/2003 | Modlin | |
| 2003/0232384 A1 | 12/2003 | Kocher et al. | |
| 2004/0002167 A1 | 1/2004 | Andersson et al. | |
| 2004/0012676 A1 | 1/2004 | Weiner et al. | |
| 2004/0023247 A1 | 2/2004 | Xu et al. | |
| 2004/0030504 A1 | 2/2004 | Helt et al. | |
| 2004/0038268 A1 | 2/2004 | Pirrung et al. | |
| 2005/0148063 A1 | 7/2005 | Cracauer et al. | |

FOREIGN PATENT DOCUMENTS

| | | |
|---|---|---|
| WO | WO 8911057 | 11/1989 |
| WO | WO 9100467 | 1/1991 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by The Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press, 1980.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices—The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry A User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

Ch Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay At Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elseviar Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

Willems, Goerge M., et al., Adsorption and Conversion of Prothrombin on a Rotating Disc, Blood, Jul. 15, 1993, vol. 82, No. 2, pp. 497-504.

U.S. Appl. No. 11/748,023, Dultz et al.

U.S. Appl. No. 11/696,369, Dultz.

U.S. Appl. No. 11/752,056, Dultz.

U.S. Appl. No. 12/125,685, Dultz.

U.S. Appl. No. 12/125,735, Dultz et al.

U.S. Appl. No. 12/650,327, Dultz et al.

* cited by examiner

APPARATUS AND METHOD FOR PERFORMING LIGAND BINDING ASSAYS ON MICROARRAYS IN MULTIWELL PLATES

FIELD OF THE INVENTION

This invention relates to an apparatus for characterizing molecular binding events for performing binding protein assays and more particularly to such systems employing multiplexing or microarrays.

BACKGROUND

U.S. Pat. No. 6,594,011 issued Jul. 15, 2003, the entirety of which is incorporated by reference herein for all purposes, discloses an imaging apparatus and method for real time imaging ellipsometry for high throughput sensing of binding events useful in molecular interaction analysis including biotech applications. The apparatus disclosed employs the immobilization of an array of binding or capture molecules ("ligands") on a horizontal planar surface of a transparent substrate and the use of a beam of polarized light directed at the underside of the surface in a manner to achieve total internal reflection (TIR) and generate an evanescent field in the plane of the ligands. The ligands are exposed to a biological sample and analytes in the biological sample bind to different patterns of the immobilized ligands in a manner to change the polarization at locations in the array at which binding occurs. An image of the array is compared with a stored image of the initial light polarization shifts to determine the location and magnitude of binding events within the array, thus identifying and quantitating the analytes present in the biological sample.

The apparatus for implementing the foregoing technique employs a prism or gratings to achieve the requisite TIR generated evanescent field, the prism being the most practical implementation.

TIR imaging ellipsometry works well for fields of view up to 1-2 cm$^2$, which permits real time imaging of tens of thousands of binding events simultaneously. However, there is a need to be able to image or scan areas which are much larger, such as 128 mm×86 mm (e.g., the area of both 384 well and 96 well plates) to permit lower costs per test and for multiple tests per patient for large numbers of patients simultaneously which is increasingly a requirement for more clinical diagnostics and personalized medicine. Obviating the need for a prism simplifies both the instrument and disposable multiwell plate.

SUMMARY

The present invention provides for immobilized ligand arrays printed on the side walls of a multiwell plate, which then allows a beam of polarized light to be directed through the transparent plate material between the wells in a manner to achieve TIR and an evanescent field in the plane of the ligands without the need to optically couple prisms or gratings to the bottom of the plate as is required in the prior art. The reflected light from the sidewall carries the binding information between analytes in a biological sample in the well and the different patterns of ligand molecules in the immobilized array. Since total internal reflection does not occur at the bottom of wells in the case where the first surface of light entry into the plate is parallel to the surface defining the well bottom which is true in a typical multiwell plate format, the realization that total internal reflection ellipsometry can be done without the use of prisms or gratings in a multiwell plate allows a cost effective solution for scaling the measurement in a way previously unimagined.

The present invention also reduces a characteristic problem in evanescent field detection technologies, which is the problem of sediment from a sample falling down onto the detection area during measurement. Applications involving open well plates require that plates are oriented with the open end upward. Having ligands at the bottom of open wells oriented in this manner exacerbates the sediment problem but this can be overcome with an array of ligands on the side wall as disclosed in the present invention. The formation of ligand arrays or a plurality of ligands on upright walls of wells and the use of imaging ellipsometry to image binding events at the arrays are thus considered to constitute a significant advance in the art.

In one embodiment, a transparent disposable multiwell plate is made by mating first and second piece parts, the first of which comprises a transparent plate with rows and columns of recesses. The second piece part comprises a transparent insert or partition which has patterns of ligand arrays immobilized on its face. A partition is inserted into slots in the first piece part in a manner to form the recesses of a row into separate wells with a ligand array facing inward into each well.

The ligand array wall, thus, is planar and preferably normal to the plane of the plate. A collimated beam of polarized light is directed through the separation between adjacent rows of cells in a manner to achieve total internal reflection (TIR) at least one well and to produce an evanescent field in the plane of the ligands on a wall in that well. An imaging system is positioned to image binding events between analytes in a sample in the well and the ligand patterns.

In another embodiment, the beam is scanned from well to well. In another embodiment, all the wells in a row are accessed simultaneously. In another embodiment, the partition is coated with a metallic film. The ligand array is immobilized on the film and the imaging system is configured for surface plasmon resonance (SPR) operation.

DETAILED DESCRIPTION

The present invention provides an advantageous apparatus and method for performing ligand binding assays using microarrays in a multiwell plate format. Prior to describing embodiments of the present invention in detail, the following definitions are provided for use throughout the present document.

Definitions

Microwell plate: A flat plate with multiple "wells" used as small test tubes. The microwell plate has become a standard tool in analytical research and clinical diagnostic testing laboratories with 6, 24, 96, 384 or even 1536 sample wells, arranged in a 2:3 rectangular matrix in one example.

Ligand: Any molecule that binds to another; in normal usage a soluble molecule such as a hormone or biological molecule that binds to a binding partner or capture molecule. The decision as to which is the ligand and which is the capture molecule is often arbitrary. In the sense of this invention, the ligand refers to the binding element attached to a planar surface and which binds to an analyte molecule in a biological sample.

Total Internal Reflection (TIR): An optical phenomenon that occurs when light strikes a medium boundary at a steep angle. If the refractive index is lower on the other side of the boundary (i.e., the side that doesn't directly receive the light) no light can pass through and effectively all of the light is reflected. The critical angle is the angle of incidence where total internal reflection begins and continues up to angles of incidence of 90 degrees.

Ellipsometry: A very sensitive optical measurement technique providing unequalled capabilities for thin film analysis utilizing the change of polarization of light which is reflected off a sample or transmitted through a sample.

Surface Plasmon Resonance (SPR): The excitation of surface plasmons by light is denoted as a surface plasmon resonance for planar surfaces. Plasmons are collective oscillations of large numbers of electrons in matter, mostly in metals.

Array: Ligands affixed to a surface at separated localized regions called spots in an ordered manner thus forming a microscopic pattern where ligand identity is determined by the location (or "address") of that particular spot.

Binding Protein (Ligand) Assay: A test that uses the binding of proteins (e.g., antibodies) to other ligands (e.g., antigens) to identify and measure the concentration of certain biological substances in blood, urine or other body components. Ligand assays may be used to diagnose disease, drug or vitamin levels, response to therapy or other information of biological relevance. Also, test results can provide information about a disease that may help in planning treatment (for example, when estrogen receptors are measured in breast cancer).

Figure 1:
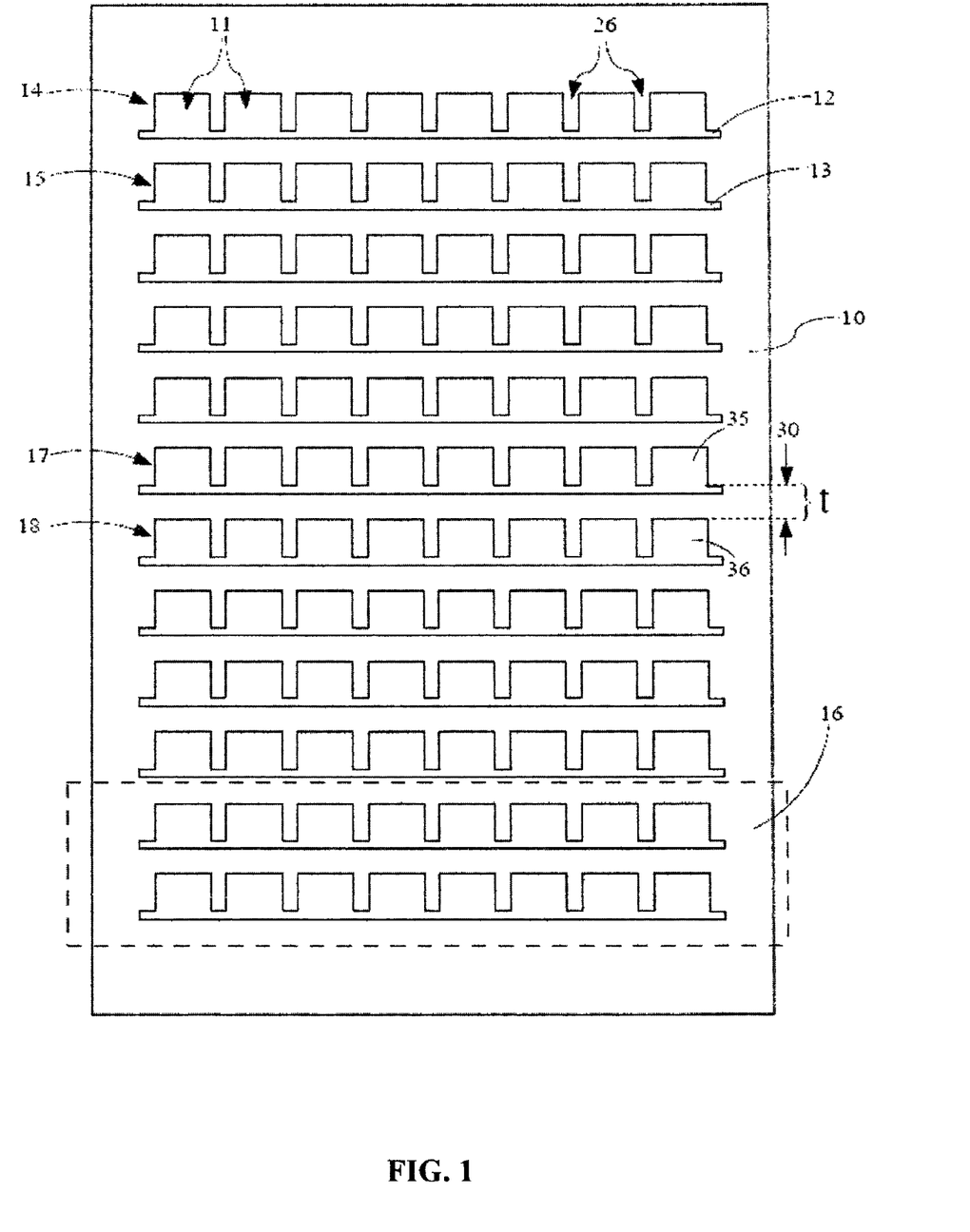
FIG. 1 is a schematic top view of a portion of a multiwell plate in accordance with an embodiment of the present invention.
Figure 2:
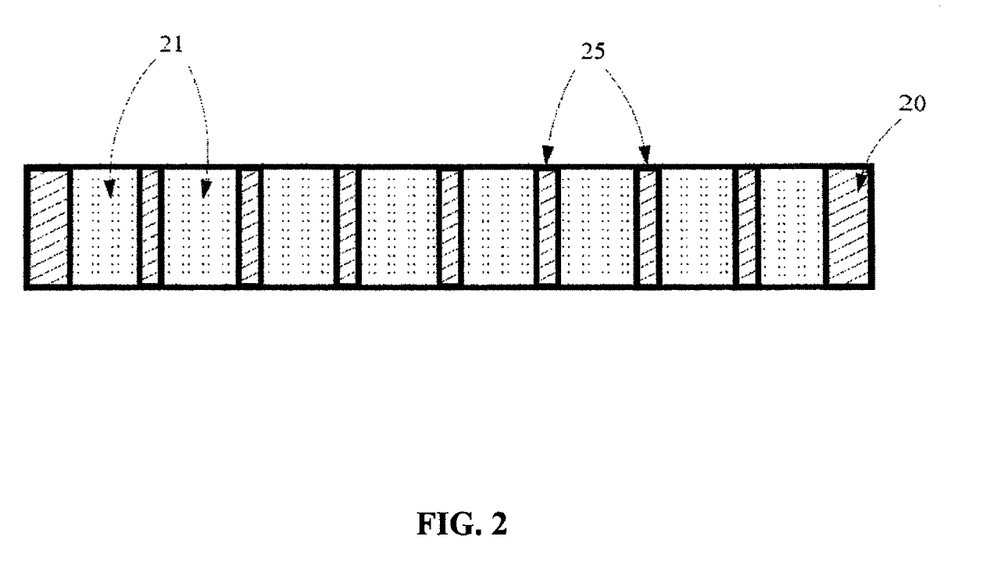
FIG. 2 is a schematic top view of another portion of a multiwell plate which mates with the portion of FIG. 1 in a way that allows index matching between both portions, in accordance with an embodiment of the present invention.

Referring now to FIG. 1, a top view of a transparent plate 10 with an array of recesses 11 arranged in rows and columns is illustrated. In one embodiment, plate 10 conveniently has the overall dimensions of a conventional multiwell plate, and in the illustrative embodiment of FIG. 1 has eight recesses in a row (forming eight columns) and twelve rows for a total of ninety-six recesses. The recesses of a row in FIG. 1 communicate with a slot, such as slots 12 and 13 for rows 14 and 15, respectively, in one example. A slot of a row may operably engage with a partition 20, which includes arrays 21 of immobilized molecules thereon, as shown in FIG. 2. Partition 20 fits securely in a slot of transparent plate 10. Multiple partitions 20 may fit in similar fashion within the rest of the rows to complete the multiwell plate structure.

FIG. 2 shows partition 20 with arrays 21 of ligands immobilized thereon. A partition as in FIG. 2 is positioned in a slot such as slot 12 of row 14 of FIG. 1 with the arrays of immobilized ligands facing into the recesses 11 of the row. The arrays of a partition in FIG. 2 can be seen to be spaced apart by spacings 25. The spacings 25 between arrays 21 correspond to protrusions 26 (FIG. 1) (made of glass or plastic, in one example) between the recesses 11 of FIG. 1. The positioning of partition 20 with plate 10 forms separated wells from recesses 11 in each row into which samples can then be placed in a procedure common to multiwell plate usage.

Figure 3A:
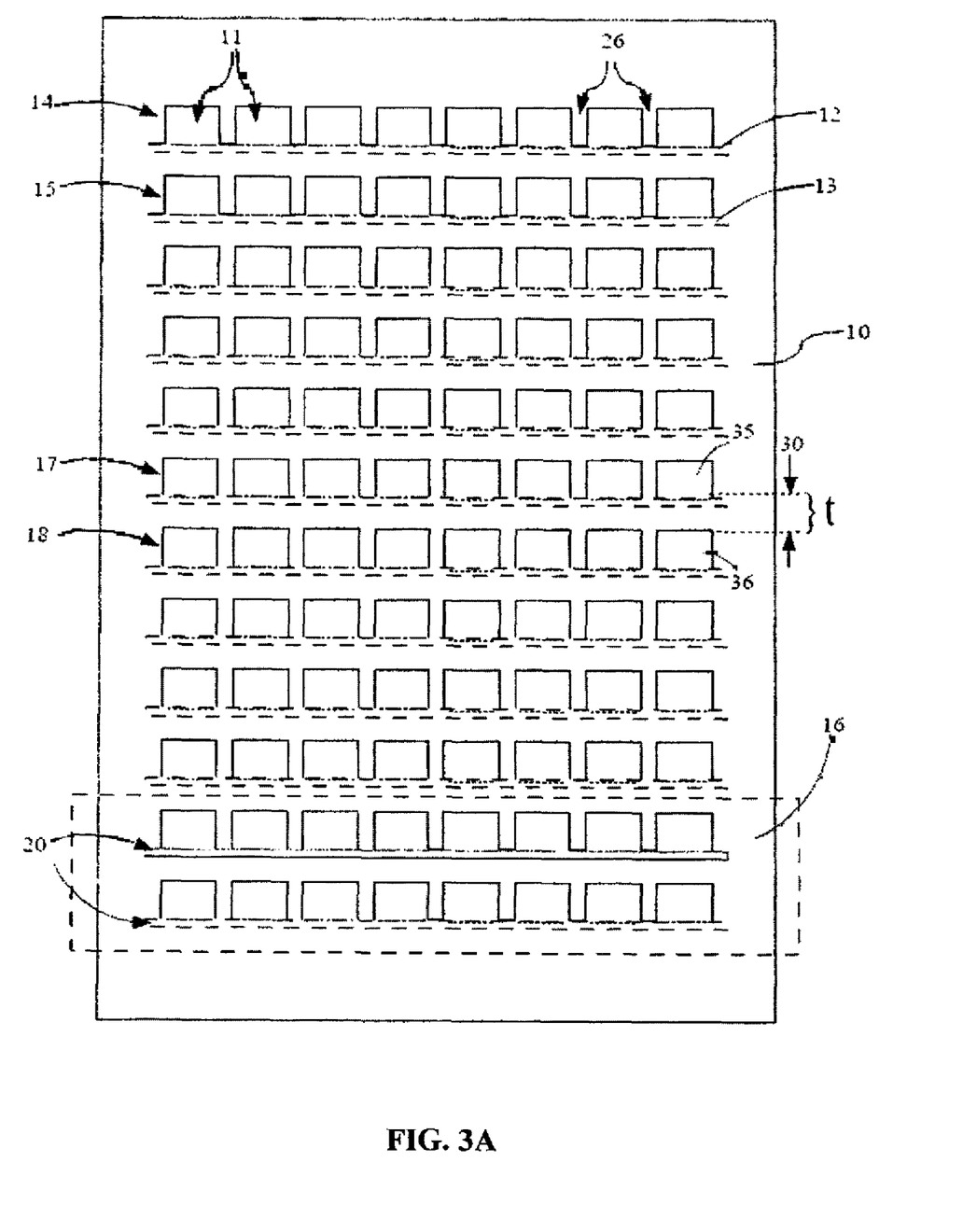
FIG. 3A is a top view of a multiwell plate formed by the assemblage of the portions of FIGS. 1 and 2 in accordance with an embodiment of the present invention.
Figure 3B:
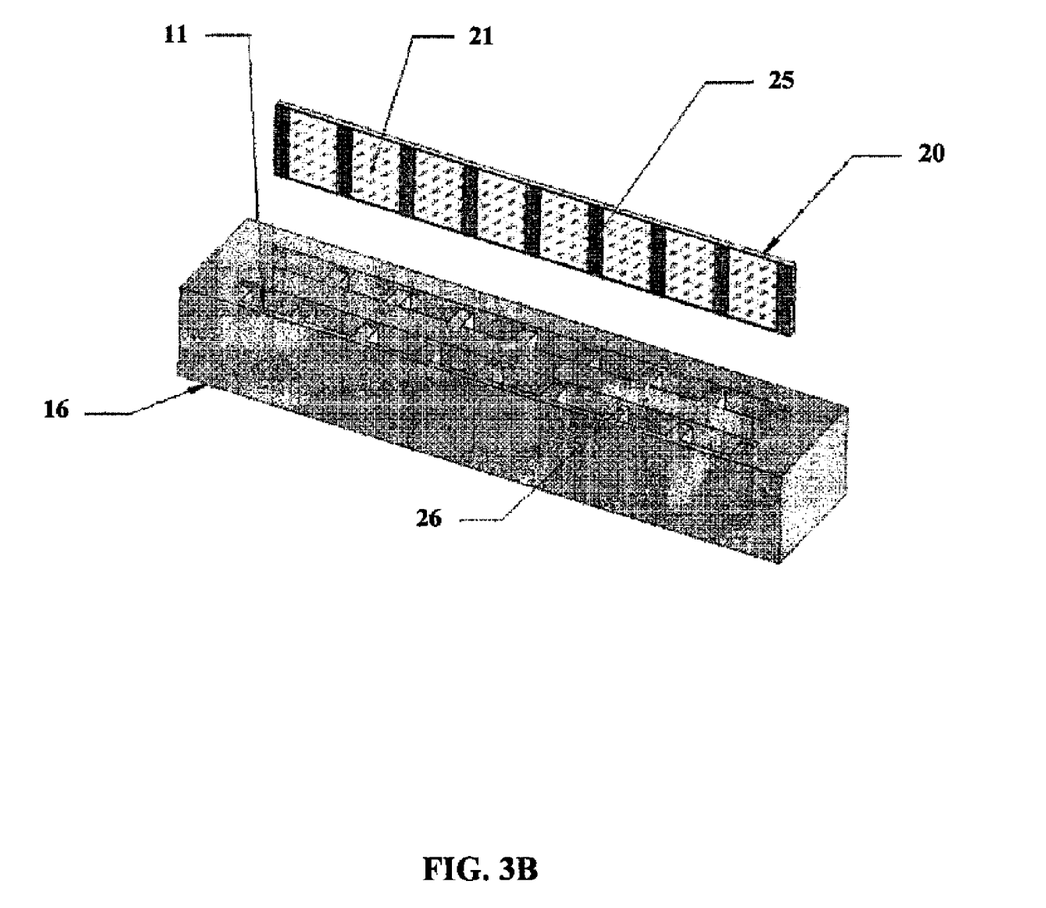
FIG. 3B is a three-dimensional exploded view of a section of a multiwell plate including the portions of FIGS. 1 and 2 in accordance with an embodiment of the present invention.
Figure 3C:
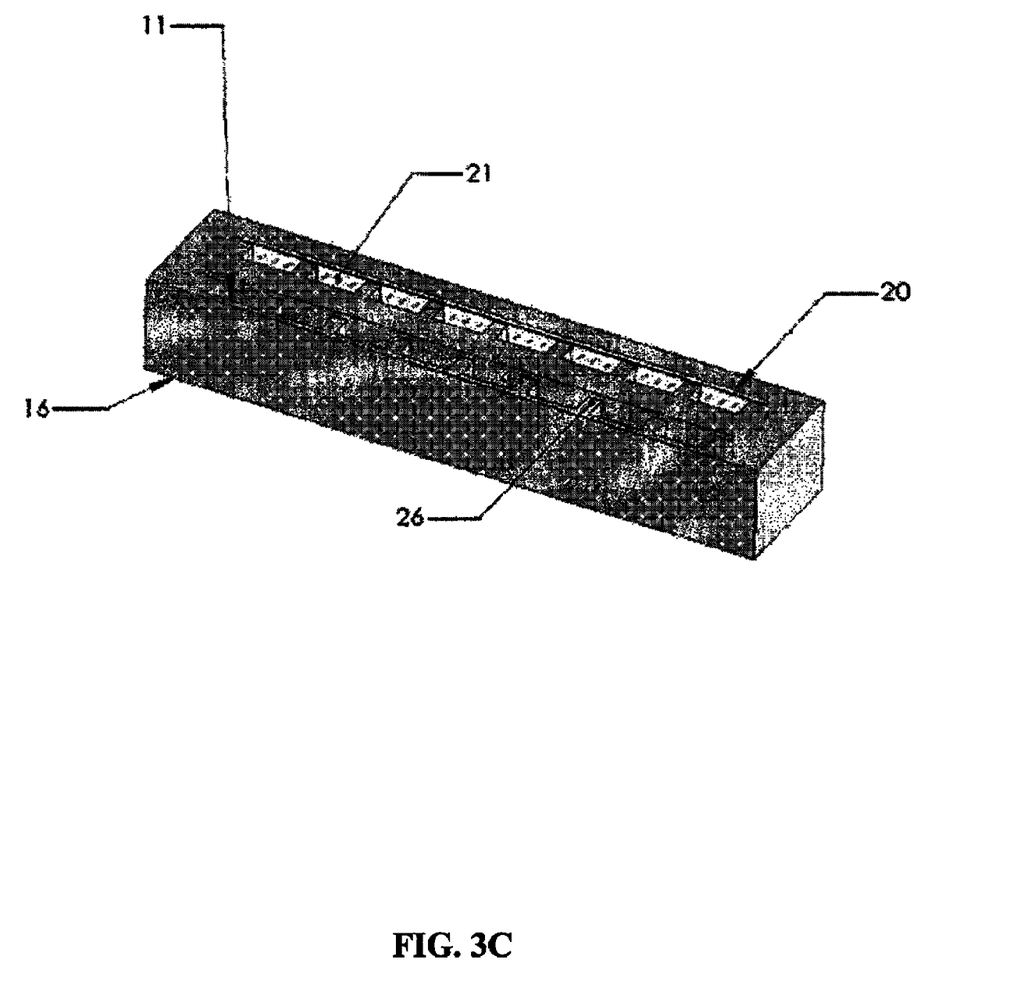
FIG. 3C is a perspective view of an assembled section of a multiwell plate in accordance with an embodiment of the present invention.

FIG. 3A illustrates a top view of a multiwell plate formed by the assemblage of plate 10 and partitions 20, FIG. 3B shows a perspective view of partition 20 of FIG. 2 positioned for insertion into a portion or section 16 of plate 10 of FIG. 1, and FIG. 3C shows a perspective view of partition 20 operably assembled with plate 10, in accordance with an embodiment of the present invention. In FIG. 3A, a partition 20 is shown as dashed lines to illustrate the partitions optically coupled to plate 10 via a material, such as a liquid or gel, placed between the two portions such that light passes without reflecting from an interface. A partition 20 is shown as solid lines prior to being optically coupled to plate 10.

In accordance with the present invention, the immobilized arrays 21 on the upright walls of the wells are exposed to analytes in the sample. The number and pattern of binding events is determined by the number of immobilized ligands and the character of those ligands in a manner disclosed, for example in U.S. Pat. No. 6,594,011, which has been previously incorporated by reference.

In order to image the binding events, the ligand array wall of partition 20 is accessed (rather than the horizontal, bottom surface as is the typical case with prior apparatus) by collimated, polarized light directed from below the plate 10 through the material between adjacent rows, such as rows 17 and 18 of FIGS. 1 and 3A, as shown by a separation 30 or "t" between the rows.

The interrogating light beam is directed at a well in a manner to achieve total internal reflection at a ligand array wall of a well so that an evanescent field is generated in the plane of the ligands immobilized on the interior face of the ligand array wall of partition 20. Binding events between analytes in the sample in the well and the immobilized ligands on the wall cause localized variations in the polarization of the light beam which can then be imaged (or scanned) by an imaging (scanning) system as illustrated in FIG. 4.

Figure 4:
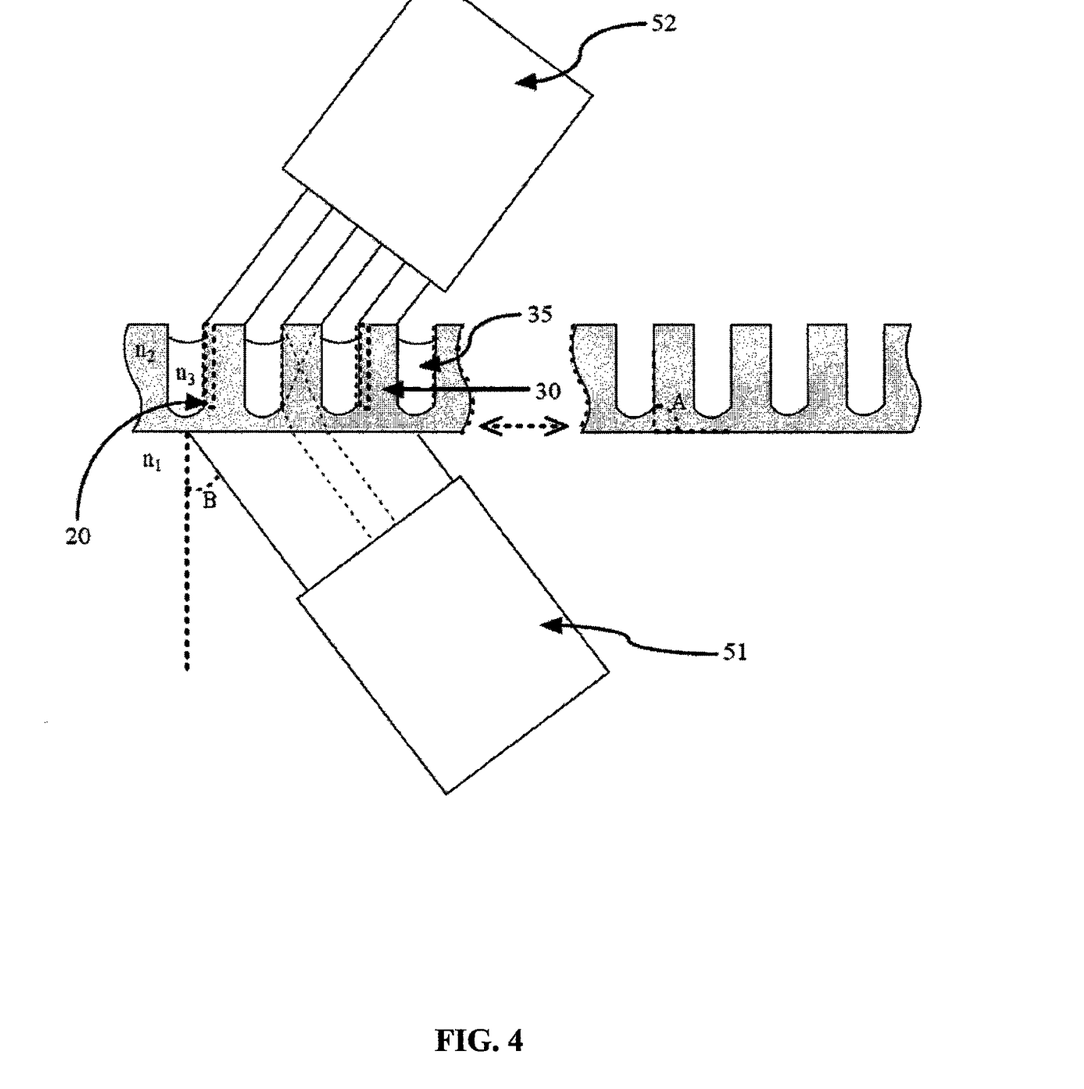
FIG. 4 is a schematic side-view representation of an interrogation and imaging system for the plate of FIGS. 1, 2, and 3.

Referring now to FIG. 4 in conjunction with FIGS. 1 through 3C, in order to achieve total internal reflection (TIR) for imaging the pattern of binding events on a wall of a well in the array of wells of FIGS. 3A-3C, the indices of refraction of the materials as well as the angle between the transmission surface and the TIR surface is important because TIR cannot occur unless the following equation is satisfied:

$$\sin(A)*\sqrt{n_2^2 - n_1^2 \sin^2(B)} - \cos(A)*n_1 \sin(B) \geq n_3$$

where A is the angle between the transmission surface contacting air and the TIR surface contacting the sample, B is the incidence angle of the light in air, $n_1$ is the index of refraction of air, $n_2$ is the index of refraction of the transparent material of the plate and $n_3$ is the index of refraction of the sample (water, blood, urine, etc.). This formula simplifies dramatically if the wall of the well is normal to the bottom of the plate since then A=90° and the second term in the above equation vanishes. The resulting equation becomes:

$$\sin(B) \leq \frac{1}{n_1} \times \sqrt{n_2^2 - n_3^2}$$

In one embodiment compatible with current multiwell plate technology, individual wells of the plate are spaced according to Ansi/SBS standards (4.5 mm center to center for 384 well plates and 9 mm center to center for 96 well plates). The plate is shown in FIG. 3A. Although the spacing of the wells is true to standard, the thickness of the separation between wells is greater in this particular embodiment. In fact, there is a minimum wall thickness in one dimension to allow total internal reflection to occur at precisely the critical angle from the side wall and this minimum wall thickness depends on the index of refraction of the plate, the index of refraction of the material inside the wells during a measurement, and the height of the wells. The formula for wall thickness is the following:

$$t \geq \frac{h\sqrt{n_2^2 - n_3^2}}{n_3}$$

where t is the wall thickness, h is the well height, $n_2$ is the index of refraction of the plate, and $n_3$ is the index of refraction of the (sample) material inside the well during measurement. For example, for plastic plates having a refractive index of 1.46, a well height of 10.67 mm, which is a typical well depth of standard plates, and a liquid sample having a refractive index of 1.34, the minimum wall thickness is about 4.62 mm, achievable for the 9 mm spacing between wells on a 96 well plate. Additionally, TIR would work for a refractive index below 1.34 for the sample material since the same angle would be in the TIR region. For polystyrene plates having a refractive index of 1.55 and the same liquid sample, the minimum thickness would be about 6.20 mm if imaging is needed all the way to the TIR angle although this is not strictly necessary.

Consider transparent strips (e.g., partitions 20) of a material with index of refraction close to or equal to the index of refraction of the plate material. These strips are planar pieces of material (FIG. 2) which may contain optical layers commonly used to optimize the sensitivity of the ellipsometric detection. The top of the optical layers may contain surface chemistry used to keep bound material stuck to the surface of the transparent material as is well understood. The partitions are inserted individually into slots (e.g., slots 12, 13 of FIG. 1) to form the sidewalls of rows of wells within the plate in such a way that a microarray of material aligns to the center of each well. Optically curing adhesive of the same refractive index as the plate may be used to coat the back surface of the plate and the region between the well partitions to thereby optically couple the two portions (as shown by partitions 20 in dashed lines in FIG. 3A). In this manner, the recesses of plate 10 are formed into wells with microarrays on the side of all wells within the plate.

FIG. 4 shows an interrogation and imaging system including a schematic representation of a portion of the plate of FIG. 3A including an illustrative pair of wells in corresponding positions in two adjacent rows of FIG. 3A. The selected wells are wells 35 and 36 of rows 17 and 18 of FIG. 3A with the separation 30 defined between them. The system of FIG. 4 includes a light source 51 and an imaging system 52 in proper positions imposing TIR, evanescent field generation, and image capture in a manner comparable to the operation as disclosed in the above identified U.S. Pat. No. 6,594,011, which has been previously incorporated in its entirety by reference.

The interrogating beam from source 51 may be directed at the (ligand) wall of a single well or simultaneously at all the (ligand) walls of all the wells in a single row of the plate of FIG. 1 by, for example, optics for shaping the beam for such operation. Moreover, the beam may be redirected by conventional implementations (e.g., MEMS) to access all the wells of each of a sequence of rows of FIG. 1, thereby allowing for scanning of the rows of wells of the multiwell plate.

In accordance with another embodiment of the present invention, the apparatus of FIGS. 1-4 can be used also in conjunction with an optical system employing surface plasmon resonance (SPR) to sense the binding events between analytes in a sample and the ligands of an array. In this embodiment, a metallic film (not shown) is formed on the face of the partition 20 of FIG. 2 and ligand arrays are immobilized on the film. In one example, the metallic film may be made of gold, silver, or copper, and is typically about 50 nm thick in the case of gold. The interrogating light beam is directed at upright ligand well walls at an angle within the TIR regime in a manner to produce surface plasmons within the metal film with a characteristic evanescent field which interacts with the plane of the array. In this embodiment, the beam angle is no longer the critical angle but the SPR angle within the TIR regime as is well understood in the field.

The disposable multiwell plate in accordance with the present invention has a number of differences and benefits over prior uses of imaging ellipsometry.

1. It is clear that the apparatus and method herein disclosed comprises a disposable multiwell plate which has dimensions compatible with robotic instrumentation currently in use with multiwell plates.
2. The disposable multiwell plate is employed similar to commercially available multiwell plates in terms of manual or automatic fluid dispensing.
3. No prism or index matching oils are necessary for the user to achieve total internal reflection.
4. Signal is far less sensitive to false readings by sediment falling out of solution.
5. Completely separate assays can be achieved within the same plate simply by rotating a multiple of 90 degrees or reading the plate from different side walls.
6. Significantly more imaging or scanning area is now achievable without the expense of the large optics (e.g., 8") otherwise required or an array of small prisms accurately aligned underneath each well or row of wells.

In the case of the imaging application, the camera itself need not be a sophisticated, high resolution CCD camera if, indeed, relatively few ligands are immobilized on each ligand wall as would be the case for most current diagnostic use. In such cases only on the order of a few to tens of ligands need be immobilized for diagnostic purposes. This lower demand for content translates to less expensive cameras and more cost-effective systems configured for doctor offices and clinical laboratories performing diagnostic testing. For other purposes such as biological research in metabolic or cancer pathways, drug target interactions in drug discovery, and biomarker profiling during clinical development of new therapeutics, higher content of ligands in arrays (100's to 1000's) may be required.

What has been described is considered merely illustrative of the invention herein and it is apparent that various modifications thereof may be devised by those skilled in the art still without departing from the spirit and scope of the invention as encompassed by the appended claims. For example, the formation of a microarray of ligands on a well wall herein may be accomplished by direct printing on a (planar) wall of a well herein rather than by printing on a partition as described herein. Also, a well need not be rectangular in shape. It need only have at least one planar wall on which ligands are immobilized. If more than one wall of a well is planar, ligands can be immobilized on more than one planar wall (e.g., by direct printing) and the plate can be reoriented with respect to the imaging system to produce the requisite TIR operation. Also, although simultaneous access of multiple ligand arrays as well as scanning from one ligand array to another have been described herein, it is contemplated that the individual spots of an array can be scanned in the manner described herein, for example, by a laser. The ligands of a microarray may also be used for multiple simultaneous tests (e.g., using different markers or ligands in a well with a single sample in a well) or for a single test (e.g., using the same markers or ligands with a single sample in a well). Different samples may also be used in different wells. Consistent with conventional multiwell plate usage, the wells may be left open or the well array may be sealed by a mating transparent plate which includes tiny openings, a pair of which is aligned with each well of the array.

What is claimed is:

1. Apparatus for performing binding ligand assays, comprising a planar transparent plate including at least one well therein, said at least one well having at least a first planar wall oriented out of the plane of said plate, the first planar wall having a plurality of ligands formed thereon in an array,
wherein said planar transparent plate includes a plurality of wells organized in rows and columns, and further wherein said rows are spaced apart a distance t given by the formula $$t \geq \frac{h\sqrt{n_2^2 - n_3^2}}{n_3}$$

wherein h is the well height, $n_2$ is the refractive index of the plate, and $n_3$ is the refractive index of a sample in the well.

2. The plate as in claim 1, wherein said first planar wall is normal to the plane of said transparent plate.

3. The plate as in claim 1, further comprising a plurality of wells organized in rows and columns, the wells of each row comprising a plurality of open ended recesses and a plurality of planar partition members each positioned to form a wall of the wells in a row, said partitions having formed thereon a ligand array in registry with each well of the associated wells of a row.

4. The plate as in claim 3, wherein one of the plurality of planar partition members may be operably coupled to a plurality of open ended recesses in a row.

5. The plate as in claim 3, wherein one of the plurality of planar partition members is integrated with the transparent plate to form a wall of the wells in a row.

6. An apparatus for sensing and/or measuring quantitatively binding events between analytes and ligands, comprising:
a first transparent planar plate having an index of refraction $n_2$ and at least one well having a height h and a wall thickness t that satisfies the following equation:

$$t \geq \frac{h\sqrt{n_2^2 - n_3^2}}{n_3}$$

wherein $n_3$ is the index of refraction of a sample in said well, said at least one well having a planar wall extending upwards from the plane of said plate and having at least one ligand immobilized thereon.

7. The apparatus as in claim 6, wherein said planar wall is normal to the plane of said plate.

8. The apparatus as in claim 6, wherein said plate comprises a plurality of wells organized in rows and columns, each of said wells having at least one planar wall extending upwards from the plane of said plate, each of said walls having at least one ligand immobilized thereon.

9. The apparatus as in claim 6, further comprising a second transparent planar plate, said second transparent planar plate being positioned with said first transparent planar plate in a manner to form at least one planar wall in each well of a row of wells, said second transparent planar plate having thereon a plurality of ligand arrays, each of said arrays being aligned with an associated one of said wells.

10. The apparatus as in claim 9, wherein said wells include a metallic film on a planar wall and the plurality of ligands is formed on said film.

11. The apparatus as in claim 10, further comprising a source of a beam of light, said source being operative to direct said beam at said walls, said apparatus also including means for changing the angle of incidence of said beam.

12. The apparatus as in claim 6, further comprising a source of a beam of collimated polarized light, said source being operative to direct said beam through said plate at said planar wall in a manner to obtain total internal reflection and to produce an evanescent field in the plane of said ligands.

13. The apparatus as in claim 12, further comprising an imaging system for imaging light reflected from said planar wall.

14. The apparatus as in claim 12, wherein said plate comprises a plurality of wells organized in rows and columns, each of said wells having at least one planar wall extending upwards from the plane of said plate, each of said walls having at least one ligand immobilized thereon, and further wherein said source is operative to direct said beam through said plate at said planar walls of said wells in a manner to obtain total internal reflection from said walls and to produce evanescent fields in the plane of said planar walls.

15. The apparatus as in claim 14, wherein said source directs light at all of the walls of all of the wells simultaneously.

16. The apparatus as in claim 15, further comprising an imaging system configured to image spatially distributed polarization changes in light reflected from said walls.

17. The apparatus as in claim 14, wherein said source directs light at the walls of said wells sequentially.

* * * * *